United States Patent [19]

Fields

[11] 3,970,658

[45] July 20, 1976

[54] NITRILE PROCESS
[75] Inventor: Ellis K. Fields, River Forest, Ill.
[73] Assignee: Standard Oil Company, Chicago, Ill.
[22] Filed: May 15, 1975
[21] Appl. No.: 577,684

[52] U.S. Cl. .................. 260/294.9; 260/283 CN; 260/296 D; 260/329 R; 260/330.5; 260/465 R; 260/465 H
[51] Int. Cl.² .................................. C07D 213/57
[58] Field of Search .................. 260/294.9, 294.8 F, 260/294.8 G, 465 R, 465 H, 329 R, 330.5, 283 CN, 329

[56] References Cited
OTHER PUBLICATIONS
Klingsberg, Pyridine and Its Derivatives, Part Three, pp. 230–237, Interscience Publishers, (1962).

Primary Examiner—Alan L. Rotman
Attorney, Agent, or Firm—William C. Clarke; Arthur G. Gilkes; William T. McClain

[57] ABSTRACT

A decarboxylation process for substituting cyano radicals for silver carboxylate radicals which comprises reacting the silver salts of carboxylic acids with silver cyanide under decarboxylation conditions of at least 320°C.

5 Claims, No Drawings

NITRILE PROCESS

BACKGROUND OF THE INVENTION

This invention relates to an economical one-step decarboxylation process to substitute cyano radicals for silver carboxylate radicals using silver salts of aromatic and heterocyclic carboxylic acids.

Usually a decarboxylation reaction results in the generation of carbon dioxide and the concurrent replacement with hydrogen on the molecule. For example, the decarboxylation of benzoic acid yields benzene and carbon dioxide. Pyridine carboxylic acid goes to pyridine and carbon dioxide. The presence of other carboxylic acid salts such as a sodium carboxylate of an aromatic acid will merely aid in the decarboxylation reaction and char to yield an ill-defined residue at best. However, the decarboxylation products using silver salts of carboxylic acids are silver, carbon dioxide and the coupled organic radicals of the silver carboxylates in the form of dimers, trimers and multiples thereof. Surprisingly also, if the decarboxylation reaction takes place in the presence of silver cyanide, the decarboxylation process forms organic nitriles of the reactant silver salt in a one-step process. The individual resulting components are readily separable by distillation due to the great differences in boiling points.

Many procedures exist for making nitriles from carboxylic acids or esters which mainly include different dehydration catalysts, temperatures and pressures. The usual process involves the conversion of the acid or ester to the amide, using an excess of ammonia which is then dehydrated to the nitrile. For example, U.S. Pat. No. 2,794,043 teaches the preparation of nitriles by reacting aliphatic acids containing 8 to 20 carbon atoms with 0.2–0.8 mole excess ammonia in the presence of a dehydration catalyst such as $Al_2O_3$, silica gel, or acid clays in the liquid phase at 200°–300°C, while removing the water from the reaction mixture by vaporization. The mixture is then subjected to vapor phase conditions at 300°–400°C in the presence of a dehydration catalyst and ammonia. This type of process is adaptable to continuous production.

A well-known modification of the procedure making nitriles from carboxylic acids is ammoxidation. In this process, a hydrocarbon such as toluene or xylene is oxidized to the acid in the presence of ammonia and oxygen with a dehydration contact catalyst at high temperatures, 400°–450°C at 5–30 psig. The nitrile is produced directly without isolation of the acid. The ammoxidation of o-xylene has been reported (Y. Ogata and K. Sokanishi, Chem. Ind. (London) 1966, 2055–56). The catalyst used was 5% $V_2O_5$ and $Al_2O_3$ with $K_2SO_4$ cocatalyst at 400°C. But ammoxidation does not work if there are more than two methyl groups on the benzene ring, nor does it work with heterocyclic compounds. The ammoxidation conditions also argue for rapid oxidation with total destruction of easily oxidized materials.

It is, therefore, a general object of my invention to provide a new process for making aromatic and heterocyclic nitriles without the necessity of converting the acid to the amide before dehydration to the nitrile or being restricted to hydrocarbons with alkyl groups in the desired cyano radical position. Another object of my invention is to provide a practical and economic process for the manufacture of heterocyclic nitrile compounds. A further object of my invention is to provide a practical and economic process for the manufacture of polyphenyl nitriles directly from monobenzenoid compounds. The nature of still other objects of my invention will be apparent from a consideration of the descriptive portion to follow.

It is my discovery that the above and other objects of the invention are attained by the silver salt/silver cyanide process herein described. I have found that the silver salts of aromatic and heterocyclic acids react with silver cyanide at elevated temperatures to produce organic nitriles. This process also gives polyphenyl nitriles directly from monobenzenoid compounds. Many of these organic nitriles which can be produced by my invented process are commercially desirable and used in commercial quantities as solvents of high dielectric and thermal stability, and as chemical intermediates.

SUMMARY OF THE INVENTION

This invention relates to a process for the production of organic nitriles which comprises the reacting of silver salts of aromatic and heterocyclic mono and polycarboxylic acids with silver cyanide at temperatures from 320° to 450°C under an inert gas in mole ratios, silver salt to silver cyanide, of 1 to 2 moles of silver cyanide for each silver carboxylate group. The reaction takes place according to the following general formula:

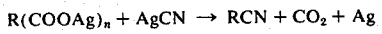

$$R(COOAg)_n + AgCN \rightarrow RCN + CO_2 + Ag$$

where R is an aromatic or heterocyclic ring and n is an integer from one to eight. R can be an aromatic radical such as phenyl, biphenyl, naphthyl, phenanthryl or anthranyl, or heterocyclic radicals of aromatic character with energy stabilization in excess of open chain and strictly cyclic analogues due to resonance. Examples are thienyl, pyridyl, benzothienyl, thienobenzenyl, quinolyl, isoquinolyl, dibenzothienyl and phenanthridyl radicals. These radicals, are represented by benzene compounds, biphenyl compounds, naphthalene compounds, phenanthrene compounds, anthracene compounds, thiophene compounds, pyridine compounds, quinoline compounds, isoquinoline compounds, benzothiophene compounds, dibenzothiophene compounds and phenanthridine compounds.

DETAILED DESCRIPTION OF THE INVENTION

Aromatic and heterocyclic nitriles are prepared in a convenient manner by reacting together the silver salts of mono and polycarboxylic acids and silver cyanide at elevated temperatures. The production of the nitrile occurs directly without intermediates. Mono and polycyano compounds as well as mono and polyphenyl compounds result from monobenzenoid compounds. Although mixtures result, the individuals are readily separated by distillation, due to typically great differences in boiling points.

For purposes of this invention, the terms "mono and disilver carboxylates" and "mono and disilver salts" are defined as those silver salts wherein the hydrogen of a carboxyl radical attached to an aromatic moiety, including a heterocyclic moiety, and combinations thereof is replaced by a silver metal ion. It is also essential for purposes of this invention that the carboxylate radicals be attached directly to the aromatic or heterocyclic ring and that there be at least one silver carboxylate group present per molecule.

"Aryl radical" is defined, for purposes of this invention, as a monovalent radical derived from an aromatic hydrocarbon. In terms of this invention, the term "aryl compounds" is defined as including aromatic compounds characterized by at least one benzene ring, i.e., either the six carbon ring of benzene or the condensed six-carbon rings of the other aromatic derivatives such as naphthalene, phenanthrene, anthracene, etc. "Aryl carboxylic acids" are defined as aromatic compounds having at least one free valence of the aryl group attached directly to the carboxylic acid group. The term "heterocyclic compound" is defined as a compound containing a cyclic or ring structure of five or more atoms in the ring in which one or more of the atoms in the ring is an element other than carbon and can be oxygen, nitrogen and/or sulfur. The term "ring compound" is defined as an organic compound whose structure is characterized by a closed ring. It is also termed a cyclic compound. Ring or cyclic compounds can be alicyclic, aromatic (or arene) and heterocyclic. The term "nitrile" refers to an organic compound containing the cyano radical, $-C \equiv N$, as the characteristic functional group.

My process for synthesizing aromatic and heterocyclic nitrile compounds from silver carboxylates has the advantages of being a one-step process and avoiding the disadvantages of alternate methods. The ammoxidation reaction to give nitriles does not work with heterocyclic compounds and specifically works with toluene, the three xylenes ($o$, $m$, $p$) and propylene. Ammoxidation does not work if there are more than two methyl groups on the benzene ring. The other processes which utilize carboxylic acids or esters require conversion to the amide and then dehydration to the nitrile.

The versatility of my novel process, that the reactants can be shelf items ready for use as needed, and its utility, inasmuch as wellknown compounds with known and demonstrated uses result from the process, add to the value of the process. The novel process can be represented by the following general equation:

$$R(COOAg)_n + AgCN \rightarrow RCN + CO_2 + Ag$$

where R is an aromatic or heterocyclic radical and $n$ is an integer from 1 to 8.

Examples of the silver salts used in my invention are silver benzoate, silver toluate, silver 2 and 3-naphthoates, silver nicotinate, silver isonicotinate, silver thiophene-2-carboxylate, silver biphenyl-4-carboxylate, silver anthraquinone-2-carboxylate, disilver terephthalate, disilver isophthalate, trisilver trimellitate, trisilver trimesate, trisilver hemimellitate, tetrasilver pyromellitate, tetrasilver mellophenate, pentasilver benzenepentacarboxylate, hexasilver mellitate, disilver salts of naphthalene 1,3-; 1,4-; 1,5-; 1,6-; 1,7-; 1,8-; 2,4-; 2,6-; and 2,7-dicarboxylic acids, tetrasilver 1,4,5,8-naphthalene tetracarboxylate, octasilver naphthaleneoctacarboxylate, disilver pyridine 2,4-; 2,5-; 2,6-; 3,5-; and 3,6-dicarboxylates, disilver thiophene-2,5-dicarboxylate, and the silver salts of di-, tri-, and tetracarboxylic acids of anthracene, anthraquinone, phenanthrene, chrysene, perylene, quinoline, isoquinoline, phenanthridine, benzothiophene (thionaphthene), dibenzothiophene, benzofuran, and dibenzofuran.

Included in the silver salts used in my invention are those of the general formula $$(AgOOC)_n - R - X - R' - (COOAg)_m$$

where R and R' are the same or different aryl or heterocyclic radicals, n and m are integers of 1 to 4, and X is a divalent atom or radical such as $-O-$, $-S-$, $-NH-$, $-CH_2-$,

$-SO_2-$, $-CH=CH-$, or $-C \equiv C-$. Examples of these silver salts are disilver diphenylether-4,4'-dicarboxylate, disilver methylene-3,3'-dibenzoate, disilver diphenylsulfone-4,4'-dicarboxylate, disilver benzophenone-4,4'-dicarboxylate, tetrasilver benzophenone-3,3',4,4'-tetracarboxylate, disilver stilbene-4,4'-dicarboxylate, and disilver diphenylacetylene-4,4'-dicarboxylate.

It is understood that the above equation is not quantitative but merely represents qualitatively the general aspects of the novel process.

If it is desired to substitute nitrile radicals for silver carboxylate radicals, the decarboxylation reaction is run by mixing the dry silver salts, as in a blender, with silver cyanide in mole ratios, silver salt to silver cyanide, which depend upon the number of carboxylic acid groups in the original organic acid. For each carboxyl group one to two moles of silver cyanide are used. A preferred ratio is 1:1 to 1.5:1 moles of silver cyanide to each carboxyl group. The solid mixture is heated in an open tube or in a bomb or in a pelleted disc under an inert gas such as nitrogen, helium or argon at 320°–450°C for 1 to 60 minutes. The lower limit of the reaction temperature of 320°C is critical as the silver cyanide must decompose for the reaction to occur. It is essential also that the silver salt used not decompose below 320°C, the decomposition temperature of silver cyanide. The upper limit of 450°C is the approximate upper limit of the decomposition temperatures of the silver salts given as examples. Most silver salts used decomposed under 400°C. Preferred conditions are 320°–400°C for 1 to 10 minutes. Products are extracted from the cooled reaction mixture by solvents such as benzene, ether or acetone. The solvent is distilled off to yield the products.

In order to facilitate a clear understanding of the invention, i.e., the novel decarboxylation process to substitute cyano radicals for silver carboxylate radicals, the following specific embodiments are described in detail. It should be understood, however, that the detailed expositions of the application of the invention, while indicating preferred embodiments, are given by way of illustration only since various changes and modifications within the spirit and scope of the invention will become apparent to those skilled in the art from this detailed description.

EXAMPLE I 2.68 Grams (0.02 mole) of silver cyanide and 2.58 grams (0.02 mole) of silver benzoate were mixed dry in a Waring blender until an intimate mixture was obtained. The mixture was transferred to an open Vycor (or quartz) tube where it was heated to 345°C for 5 minutes under nitrogen flowing at 30 cc/minute. The distillate was caught in a cooled receiving flask. The distillate and the cooled solid residue were extracted with two 100 ml. portions of ether. The filtered ether solution was distilled to obtain a residue of 0.5 grams. Analysis of the residue by gas chromatography and mass spectroscopy was: 12% benzonitrile, 57% biphenyl, 7.5% cyanobiphenyl, 20% terphenyl, and 3.5% cyanoterphenyl.

EXAMPLE II 11.4 Grams (0.03 mole) of disilver phthalate and 10.64 grams (0.08 mole) of silver cyanide were intimately mixed as in Example I. The mixture was placed in a bomb and heated at 320°–350°C for one hour. The cooled bomb contents were extracted with two 100 ml. portions of acetone. The filtered acetone solution was distilled to obtain a 2.4 gram residue that analyzed 42% benzonitrile, 25% biphenyl, 28% cyanobiphenyl, and 5% dicyanobiphenyl. Analysis was by gas chromatography and mass spectroscopy.

EXAMPLES III–VII

In the following examples, intimately mixed mixtures of the silver salts were pelleted into discs at 10,000 psi using a Buehlen Mounting Press pelletizer. The compressed discs were then heated in a Vycor open tube under nitrogen flowing at 30 cc/minute. The cooled mixture was extracted in each example with two 100 ml. portions of ether or acetone. The filtered solution in each example was then distilled to the dry residue which was analyzed by gas chromatography and mass spectroscopy. The data in each example are in Table I.

What is claimed is:

1. A decarboxylation process for substituting cyano radicals for silver carboxylate radicals which comprises reacting the silver salt of a carboxylic acid with silver cyanide under decarboxylation conditions at a temperature of at least 320°C–450°C, the said silver carboxylate salt being selected from the group consisting of silver salts of benzene compounds, biphenyl compounds, naphthalene compounds, phenanthrene compounds, anthracene compounds, thiophene compounds, pyridine compounds, quinoline compounds, isoquinoline compounds, benzothiophene compounds, dibenzothiophene compounds and phenanthridine compounds; said silver carboxylate radicals are from 1 to 4 in number.

2. The process of claim 1 wherein the said silver salt is a salt of a heterocyclic carboxylic acid selected from the group consisting of disilver pyridine-3,5-, dicarboxylate and disilver thiophene-2,5-dicarboxylate.

3. The process of claim 1 wherein said silver salt of an aromatic carboxylic acid is selected from the group consisting of silver benzoate, disilver phthalate, disilver isophthalate, trisilver trimellitate and trisilver trimesate.

4. The process of claim 1 wherein said decarboxylation conditions comprise temperatures of 320°–450°C under an inert gas.

5. The process of claim 1 wherein said silver salts are reacted with silver cyanide in mole ratios, silver salt to silver cyanide, said ratio comprising one to two moles of said silver cyanide per number of silver carboxylate groups of said silver salts.

Table I

Examples III–VII - Data and Analyses

| Example | Temp °C /Minutes | Wgt. Grams | Products | Analyses % |
|---|---|---|---|---|
| III | | | | |
| Disilver Isophthalate | 400°C/5 | 0.3 | Benzonitrile | 55 |
| 1.9 Grams (0.01 mole) | | | Isophthalonitrile | 10 |
| Silver Cyanide | | | Bisphenyl | 9 |
| 2.68 Grams (0.02 mole) | | | Cyanobiphenyl | 16.5 |
| (Extracted with ether) | | | Dicyanobiphenyl | 5.5 |
| | | | Cyanoterphenyl | 5 |
| IV | | | | |
| Trisilver Trimellitate | 400°C/5 | 0.3 | Benzonitrile | 13 |
| 2.66 Grams (0.005 mole) | | | Dicyanobenzene | 37 |
| Silver Cyanide | | | Trimellitic Acid | |
| 2.01 Grams (0.015 mole) | | | Trinitrile | 7 |
| (Extracted with acetone) | | | Cyanobiphenyl | 12 |
| | | | Dicyanobiphenyl | 22 |
| | | | Tricyanobiphenyl | 9 |
| V | | | | |
| Trisilver Trimesate | 350°C/5 | 0.4 | Benzonitrile | 18 |
| 2.66 Grams (0.005 mole) | | | Isophthalonitrile | 41 |
| Silver Cyanide | | | 1,3,5-tricyanobenzene | 8 |
| 2.01 Grams (0.015 mole) | | | Cyanobiphenyl | 11 |
| (Extracted with 100 ml. | | | Dicyanobiphenyl | 14 |
| ether and 2-100 ml. acetone) | | | Tricyanobiphenyl | 8 |
| VI | | | | |
| Disilver Pyridine-3,5-Di- | 400°C/5 | 0.6 | Pyridine | 23 |
| carboxylate | | | Nicotinonitrile | 32 |
| 1.91 Grams (0.005 mole) | | | 3,5-Dicyanopyridine | 4 |
| Silver Cyanide | | | Bipyridyl | 30 |
| 1.34 Grams (0.01 mole) | | | Cyanobipyridyl | 11 |
| (Extracted with acetone) | | | | |
| VII | | | | |
| Disilver Thiophene-2,5-di- | 400°C/5 | 0.3 | Thiophene | 27 |
| carboxylate | | | 2-Cyanothiophene | 19 |
| 1.93 Grams (0.005 mole) | | | Bithienyl | 49 |
| Silver Cyanide | | | Cyanobithienyl | 5 |
| 1.34 Grams (0.01 mole) | | | | |
| (Extracted with acetone) | | | | |

* * * * *

UNITED STATES PATENT OFFICE
CERTIFICATE OF CORRECTION

Patent No. 3,970,658　　　　　　　　　　Dated July 20, 1976

Inventor(s) Ellis K. Fields

It is certified that error appears in the above-identified patent and that said Letters Patent are hereby corrected as shown below:

Column 5, line 40, "bisphenyl" should read -- biphenyl --.

Signed and Sealed this

Twenty-sixth Day of October 1976

[SEAL]

Attest:

RUTH C. MASON
*Attesting Officer*

C. MARSHALL DANN
*Commissioner of Patents and Trademarks*